United States Patent
Säfström

(10) Patent No.: US 6,203,326 B1
(45) Date of Patent: Mar. 20, 2001

(54) DENTAL JEWELRY

(75) Inventor: Kent Säfström, Märsta (SE)

(73) Assignee: Echodent AB, Marsta (SE)

( * ) Notice: Subject to any disclaimer, the term of this patent is extended or adjusted under 35 U.S.C. 154(b) by 0 days.

(21) Appl. No.: 09/404,767

(22) Filed: Sep. 24, 1999

(51) Int. Cl.[7] .................................................. A61C 13/08
(52) U.S. Cl. ............................................ 433/229; 433/206
(58) Field of Search .................... 433/229, 206, 433/207, 8, 9

(56) References Cited

U.S. PATENT DOCUMENTS

| | | | |
|---|---|---|---|
| 4,243,386 | 1/1981 | Kawaguchi | 433/9 |
| 4,322,206 | 3/1982 | Reynolds | 433/9 |
| 4,544,353 | 10/1985 | Maurer et al. | 433/9 |
| 4,992,297 | 2/1991 | van der Zel | 427/2 |
| 5,104,320 * | 4/1992 | Stoll | 433/206 |
| 5,267,855 | 12/1993 | Tuneberg | 433/9 |
| 5,295,823 | 3/1994 | Farzin-Nia | 433/9 |
| 5,480,301 | 1/1996 | Farzin-Nia et al. | 433/9 |
| 5,522,725 | 6/1996 | Jordan et al. | 433/9 |
| 5,622,494 | 4/1997 | Andreiko et al. | 433/9 |
| 5,711,665 * | 1/1998 | Adam et al. | 433/9 |
| 5,782,638 | 7/1998 | Warren, III et al. | 433/206 |
| 5,810,593 | 9/1998 | White et al. | 433/206 |

* cited by examiner

Primary Examiner—John J. Wilson
Assistant Examiner—Melba Bumgarner
(74) Attorney, Agent, or Firm—Patterson, Thuente, Skaar & Christensen, P.A.

(57) ABSTRACT

Dental jewelry includes a surface-covering jewelry piece, the body of which is designed to lie principally in a plane parallel with the tooth surface and is designed to be affixed to said surface by a layer of fixing composite. On its backside, which is designed to be turned toward the surface of the tooth, the jewelry piece has a recess which, along the piece's circumference of said backside, defines a continual supporting edge upon which the jewelry piece rests against the tooth surface.

17 Claims, 1 Drawing Sheet

DENTAL JEWELRY

CROSS-REFERENCE TO RELATED APPLICATION

The subject matter of this application is related to the subject matter of Swedish Patent Application No. P7403SE, filed on or about Jan. 7, 1998, which is incorporated by reference herein in its entirety.

BACKGROUND OF THE INVENTION

Dental jewelry is in and of itself previously known and consists usually of a small, thin, considerably flat piece, usually of precious metal such as gold. The piece can have a surface area, by way of example, of 2×2 mm, and a thickness, by way of example, of 0.5 mm. Such heretofore known dental jewelry is fastened upon the surface of the tooth with a fixing composite. In order to improve the dental jewelry's bonding to the tooth surface, it is common to provide for special carved-out formations in the dental jewelry's backside which are spread across said backside in order to promote a form fitting attachment between a hardening layer of the fixing composite and the dental jewelry.

One problem with the dental jewelry of the referenced art is the risk that an exposed fissure might remain between the dental jewelry and the tooth surface, into which, by way of example, bacteria could enter and cause discoloration or injuries to the surface of the tooth.

Another problem is that the bond of the jewelry to the surface of the tooth may become relatively weak as a result of, for example, the application of shearing forces within the plane of the tooth surface.

SUMMARY OF THE INVENTION

Thus, an object of the invention is to provide a type of dental jewelry with which said problems can be avoided or limited either wholly or partially.

The invention is characterized in principle in that the dental jewelry is designed to contain on the backside a recess which extends around the dental jewelry's circumferential edge and defines a continual circumferential edge, which lies principally within a plane for the purpose of resting against the surface of the tooth.

In the preferred form of design, the recess is bowl-shaped, so that the central portion of the dental jewelry's backside is concave. In the preferred form of design, the jewelry is designed on its external side in such a manner that in the vicinity of its circumferential part it is sloped at an angle downwardly and outwardly.

The backside of the jewelry is representatively rough and/or provided with formations such as pits, notches, etc., which have a width of a few hundredths of a millimeter. These may even have a depth of the same order of size. As an example, such indentations can have a radius of between approximately $1/100$ and $2/100$ of a millimeter.

In order to affix the dental jewelry, a layer of fixing agent (also known as composite) that is capable of hardening is spread across the surface of a tooth over an area which is slightly larger than the area of the dental jewelry piece, whereafter the piece of dental jewelry is pressed downward into this layer of composite. Thereafter, the remaining composite is scraped away around the jewelry piece's circumference, wherewith, however, a fissure between the dental jewelry's circumferential edge portion and the surface of the tooth is left filled with the composite. The composite filled fissure can then be made smooth by means of grinding, for example, subsequent to the hardening of the composite.

Due to the dental jewelry's backside having a concave recess, the thickness of the jewelry's material can be made significantly less than the jewelry's height above the surface of the tooth. This means that the dentist or other individual performing the affixation can bend the jewelry with the exertion of limited pressure so that its supporting edge is fitted to the tooth's surface/foundation's curvature in the desired position of the jewelry. In this manner, one can minimize the fissure between the tooth's surface and the jewelry's supporting edge. Subsequently, when the jewelry is bonded to the fixing medium/composite, the solidified composite is able to provide for the stabilization of the jewelry.

The jewelry, as described in the invention, in certain cases, is mounted for the purpose of providing decoration for a limited period of time, wherein, thus, the jewelry is removed after a certain time frame. In such circumstances, it is, of course, important that no discoloration or other damage occur to the tooth surface.

In certain forms of design, the recess's peripheral area, which is adjacent to the jewelry's supporting edge, can be made to slope towards the plane into which the supporting surface of the jewelry extends. This inner edge part, in one manner of construction, slopes at an angle downwardly and outwardly toward the plane/edge part. In another form of construction, the aforementioned edge part can slope at an angle, either completely or partially, downwardly/inwardly in order to form a carved-out surface, which is intended to be embedded in the layer of composite. The jewelry's principal continuing edge part, which rests against the tooth surface, can be relatively thin and therefore relatively easily deformable for the purpose of being able to form such in a ductile manner in order to achieve a better bond to the tooth surface around the jewelry's circumference.

By means of the peripheral portion of the recess sloping at an angle downwardly/outwardly against the jewelry's supporting plane (the tooth surface), said surface acts to bring forth a displacement of the composite within the recess with its circumference in contact with the jewelry's embedment in the composite. In this manner, it is ensured that the composite is brought into close surface contact against the recess's inner surface in its circumferential part, and further that the composite in the vicinity of the recess's circumferential part, is forced substantially against the recess's bottom with the circumferential part still inside of the recess's more centrally located part (with the assumption that the composite will not completely fill out the recess, and with the further assumption that the recess will spread itself out over essentially the entire underside of the jewelry).

BRIEF DESCRIPTION OF THE DRAWINGS

Embodiments of the invention will be described below in model form with references to the attached drawings.

DETAILED DESCRIPTION OF PREFERRED EMBODIMENTS

Figure 1:
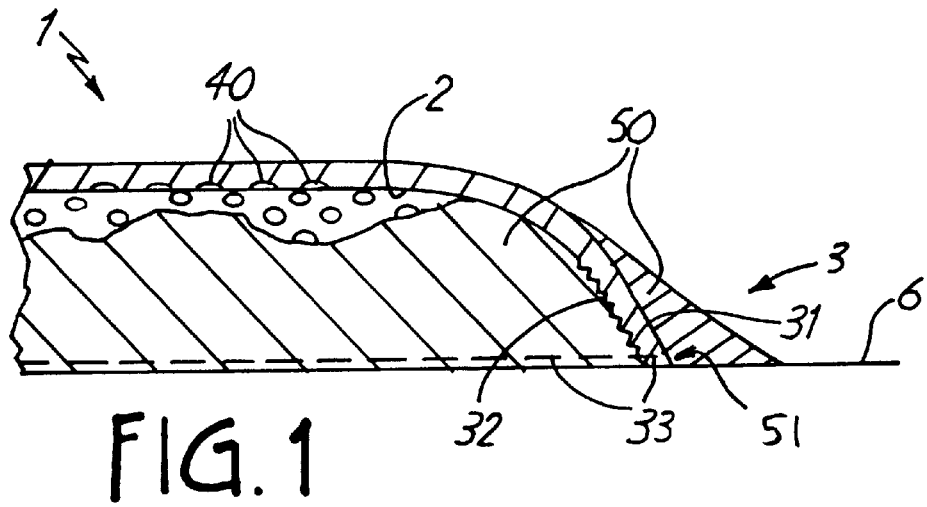
FIG. 1 shows a cross-sectional view of the dental jewelry when affixed to a tooth.
Figure 2:
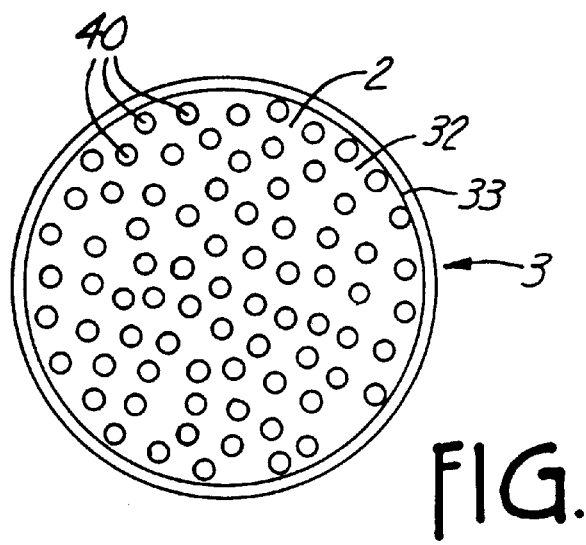
FIG. 2 shows a top plan view of the dental jewelry's backside.

Referring to FIG. 1, there is shown an axial view through the dental jewelry 1 in accordance with the invention, when affixed principally to a flat tooth surface 6. The jewelry 1, has a concave recess 2 on the side which is turned against the tooth surface 6 which extends across essentially the entire backside of the jewelry 1. The jewelry 1, in this manner, has a circumferential piece 3 whose outer wall 31 and inner wall 32 both slope at an angle downwardly and outwardly. The jewelry 1 rests against the foundation surface 6 with a surface edge 33 that is essentially continual.

The recess's 2 surface exhibits a multiplicity of indentations 40 with a radius, by way of example, of between approximately $1/100$ and $2/100$ of a millimeter.

In order to affix the jewelry 1 to the tooth surface 6, a layer of composite 50 capable of hardening is applied in a layer over the tooth surface 6 in the area where the jewelry 1 will be placed. The jewelry 1 is pressed into the composite 50 until the supporting edge 33 lies, in essence, against the tooth surface 6. The layer of composite 50 can have such thickness so that the concave recess 2 on the jewelry's 1 backside is filled to a significant extent with the recess's 2 overhead clearance. In FIG. 1, the recess 2 is shown nearly filled of composite 50.

When the jewelry 1 is pressed down into the layer of composite, the composite in the vicinity of the sloping wall surface 32 is displaced upwardly and inwardly, wherein the composite 50 is brought into close contact with the wall surface 32, and is raised to an increased level in an area radially inside of the sloping inner wall part 32.

The composite material 50 outside of the jewelry's outer circumferential wall 31 is scraped off around the jewelry's 1 circumference, causing the formation of an excess in the fissure 51 between the tooth surface 6 and the wall surface 31.

Upon the hardening of the composite 50 the excess in the crevice 51 can be ground away.

Because the jewelry 1 has a relatively low wall thickness, due to the recess 2 on the underside, the jewelry 1 can be formed in a ductile manner so that the essentially continual supporting edge 32 is placed in a configuration which closely bonds to the tooth surface's 6 configuration along the supporting edge 32. In this way, the fissure between the jewelry's supporting surface 33 and the tooth surface 6 is minimized. By FIG. 1 it is understood that the tooth jewelry 1 is securely fastened as against its shifting on the plane of the tooth surface 6. In addition, as a result of the jewelry's 1 being pressed down into the composite material 50, a relationship is realized wherein the edging between the supporting surface 33 and the tooth surface 6 becomes lesser and is much more likely to be filled in and sealed by the composite material 50. Moreover, by means of the filling in of the fissure 51 additional security is ensured in relation to the formation of cracks in which bacteria and the like can enter and cause discoloration and injury to the surface of the tooth 6.

Figure 3:
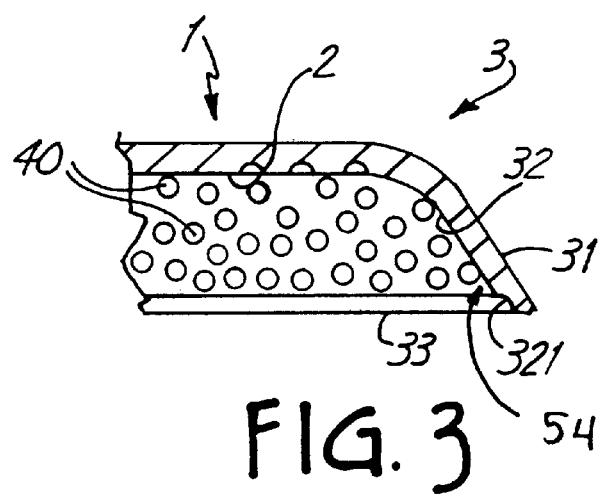
FIG. 3 shows a cross-sectional view of an alternative construction of the dental jewelry.

By FIG. 3 one understands that a modification is set forth, wherein the recess's 2 peripheral wall surface 32 has a surface section 321 which slopes at an angle downwardly/inwardly to form a carved-out surface 54 which is intended to lie embedded in the layer composite 50 within the recess 2.

While the invention has been described with reference to specific embodiments, the description is intended to be illustrative and is not to be construed as limiting the scope of the invention. Various modifications and changes will be apparent to those skilled in the art without departing from the spirit and scope of the invention.

What is claimed is:

1. Dental jewelry for attachment to a tooth surface, the dental jewelry comprising:

an inner surface that defines a concave recess;
an outer surface;
a surface edge that extends between the inner surface and the outer surface and rests substantially against the tooth surface when the dental jewelry is attached to the tooth surface; and
an inwardly directed surface that extends from the inner surface proximate the surface edge and thereby defines a carved-out region.

2. Dental jewelry of claim 1, wherein the inner surface is rough for increasing a bond between the dental jewelry and a fixing composite used to attach the dental jewelry to the tooth surface.

3. Dental jewelry of claim 2, wherein the inner surface has a plurality of indentations formed therein, wherein the plurality of indentation each have a radius of several hundredths of a millimeter.

4. Dental jewelry of claim 1, wherein the outer surface proximate the surface edge is oriented downwardly and outwardly from a center of the outer surface.

5. Dental jewelry of claim 1, wherein the inner surface proximate the surface edge and the inwardly directed surface is oriented downwardly and outwardly from a center of the inner surface.

6. Dental jewelry of claim 1, wherein the dental jewelry is fabricated from a ductile material.

7. Dental jewelry for attachment to a tooth surface, the dental jewelry comprising:

an inner surface that defines a concave recess;
an outer surface; and
an inwardly directed surface that extends from the inner surface proximate an intersection of the inner surface and the outer surface and thereby defines a carved-out region.

8. Dental jewelry of claim 7, wherein the inner surface is rough for increasing a bond between the dental jewelry and a fixing composite used to attach the dental jewelry to the tooth surface.

9. Dental jewelry of claim 8, wherein the inner surface has a plurality of indentations formed therein, wherein the plurality of indentation each have a radius of several hundredths of a millimeter.

10. Dental jewelry of claim 7, wherein the outer surface proximate the intersection of the inner surface and the outer surface is oriented downwardly and outwardly from a center of the outer surface.

11. Dental jewelry of claim 7, wherein the inner surface proximate the inwardly directed surface is oriented downwardly and outwardly from a center of the inner surface.

12. Dental jewelry of claim 7, wherein the dental jewelry is fabricated from a ductile material.

13. A method of mounting dental jewelry to a tooth surface, the method comprising:

forming the dental jewelry with an inner surface, an outer surface, an edge surface and an inwardly directed surface, wherein the inner surface defines a concave recess, wherein the edge surface extends between the inner surface and the outer surface, and wherein the inwardly directed surface extends from the inner surface proximate the surface edge and thereby defines a carved-out region;
substantially filling the concave recess with a fixing composite; and
placing the dental jewelry adjacent the tooth surface so that the surface edge rests substantially against the tooth surface and so that the fixing composite bonds the dental jewelry to the tooth surface.

14. The method of claim 13, wherein the outer surface proximate the edge surface is oriented downwardly and outwardly from a center of the outer surface, and wherein the fixing composite at least partially extends over the outer surface proximate the edge surface.

15. The method of claim 13, and further comprising forming the inner surface with a rough texture to increase a bond between the dental jewelry and the fixing composite.

16. The method of claim 13, and further comprising forming a plurality of indentations in the inner surface.

17. The method of claim 13, wherein the carved-out region is substantially filled with the fixing composite when the dental jewelry is placed adjacent the tooth surface.

\* \* \* \* \*